United States Patent [19]

Keith et al.

[11] 4,014,898

[45] Mar. 29, 1977

[54] N,N-DIALKYLAMINOETHOXYETHYLPH-THALIMIDOMALONATES

[75] Inventors: Dennis Keith, Montclair; Manfred Weigele, North Caldwell, both of N.J.

[73] Assignee: Hoffmann-La Roche Inc., Nutley, N.J.

[22] Filed: Mar. 18, 1975

[21] Appl. No.: 559,602

Related U.S. Application Data

[62] Division of Ser. No. 457,340, April 3, 1974, Pat. No. 3,887,615.

[52] U.S. Cl. .............................. 260/326 N; 71/68; 71/113; 260/247.2 B; 260/293.88
[51] Int. Cl.$^2$ ...................................... C07D 209/34
[58] Field of Search ............................. 260/326 N

[56] References Cited

OTHER PUBLICATIONS

Black et al., "Chem. Abstracts," vol. 77, (1972) No. 127024f.

*Primary Examiner*—Henry R. Jiles
*Assistant Examiner*—R. W. Ramsuer
*Attorney, Agent, or Firm*—Samuel L. Welt; George M. Gould; Frank P. Hoffman

[57] ABSTRACT

Novel butanoic acid derivatives, bearing an ether grouping in the 4-position are disclosed, together with processes for the preparation of these compounds. These novel compounds inhibit ethylene production in plant tissues and therefore have utility as agents to retard the ripening of fruit during shipment and to prolong the life of cut flowers, and to prevent premature bud break in commercial fruit trees, thus avoiding frost kill.

1 Claim, No Drawings

N,N-DIALKYLAMINOETHOXYETHYLPHTHALIMIDOMALONATES

This is a division of application Ser. No. 457,340 filed Apr. 3, 1974 — DAVID D. KEITH and MANFRED WEIGELE — NOVEL BUTANOIC ACID DERIVATIVES, now U.S. Pat. No. 3,887,615.

DETAILED DESCRIPTION OF THE INVENTION

The present invention is directed to novel butanoic acid derivatives bearing an ether group in the 4-position, and to methods for preparing these compounds. More particularly, the present invention relates to compounds of the formula

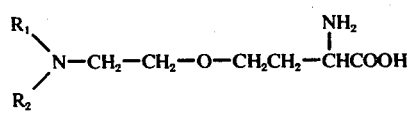

wherein $R_1$ and $R_2$ each independently represent hydrogen or lower alkyl, or $R_1$ and $R_2$ taken together with their attached nitrogen atom form a 5- or 6-membered saturated heterocyclic ring which may contain an additional nitrogen atom or an oxygen atom;
provided that one of $R_1$ or $R_2$ is other than hydrogen the pharmaceutically acceptable addition salts thereof, and the optical antipodes thereof.

As used throughout this disclosure, the term "lower alkyl" signifies straight and branched chain hydrocarbon groups containing from 1 to 7, preferably from 1 to 4, carbon atoms, such as methyl, ethyl, propyl, and the like. The term "lower alkanoyl" denotes a -CO-lower alkyl group such as acetyl, propionyl, butyryl and the like. The term "halogen" signifies all four forms thereof, ie. chlorine, bromine, fluorine and iodine unless specified otherwise.

Preferred among the compounds of formula I above are those wherein $R_1$ signifies lower alkyl and $R_2$ signifies hydrogen or lower alkyl, i.e. compounds of the formula

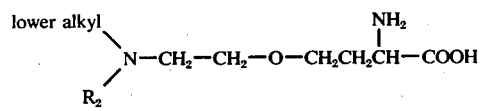

wherein $R_2$ signifies hydrogen or lower alkyl
the pharmaceutically acceptable addition salts thereof, and the optical antipodes thereof.

If $R_1$ and/or $R_2$ signify lower alkyl, ethyl is preferred. Examples of the 5- or 6-membered saturated heterocyclic rings which can be formed by $R_1$ and $R_2$ taken together with their attached nitrogen atom include pyrrolidino, piperazino, morpholino, and piperidino.

The compounds of formula I above may be prepared by reacting a bis-[haloethyl]ether of the formula

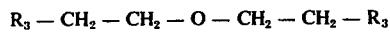

wherein $R_3$ signifies chlorine, bromine or iodine with the alkali metal salt, preferably the sodium salt, of a di-lower alkyl-N-$R_4$-malonate of the formula

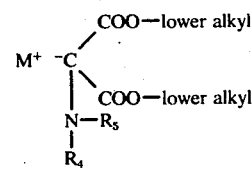

wherein $M^+$ represents an alkali metal ion, $R_4$ is a suitable nitrogen protecting group, $R_5$ is hydrogen, or $R_4$ and $R_5$ taken together with their attached nitrogen atom form the phthalimido group.

The reaction between the ether of formula II and the malonate of formula III yields a compound of the formula

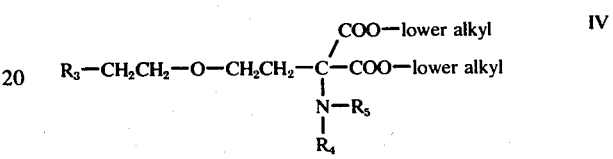

wherein $R_3$, $R_4$ and $R_5$ are as described above.

Suitable nitrogen protecting groups for the purposes of the above discussed reaction include acyl groups such as acetyl or benzoyl, sulfonyl groups such as mesyl or tosyl, the carbobenzoxy group and the like.

If the $R_3$ substituent signifies chlorine, it may be expedient to add potassium iodide to the reaction mixture so that the more reactive iodide ion replaces the chlorine ion.

The reaction between the compounds of formulae II and III above is preferably effected in the presence of a polar organic solvent. Suitable solvents for this purpose include dimethylformamide, dimethylsulfoxide, hexamethylphosphoramide and the like. Temperature is not critical to this reaction, the temperature employed depending primarily on the reagents being used; temperatures in the range of room temperature to the reflux temperature of the reaction medium are appropriate.

The compound of formula IV thus obtained is then reacted with a primary or secondary amine of the formula

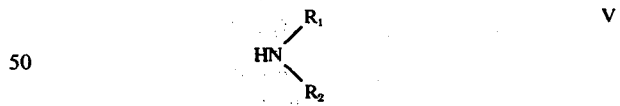

wherein $R_1$ and $R_2$ are as described above.

This reaction between the compounds of formulae IV and V results in replacement of the $R_3$ group of the formula IV compound with a substituted amino group to yield a compound of the formula

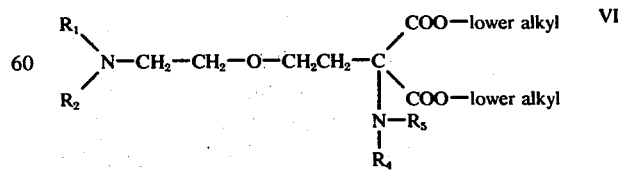

wherein $R_1$, $R_2$, $R_4$ and $R_5$ are as described above.

If, in the compound of formula IV, the nitrogen protecting group is a phthalimido group, and, if in the compound of formula V, $R_1$ is lower alkyl and $R_2$ is hydrogen, the reaction between these two compounds results not only in replacement of the $R_3$ group but also in the opening of the phthalimido ring to yield an intermediate of the formula

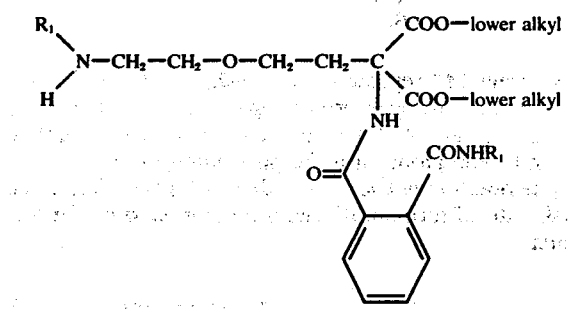

VII wherein $R_1$ is as described above.

The reaction between the compound of formula IV and the amine of formula V above may be conducted using an excess of the amine as the solvent system. Alternatively, this reaction may be conducted in the presence of an inert organic solvent. Suitable solvents for the purpose include halogenated hydrocarbons such as methylene chloride and the like, ether, and aromatic hydrocarbons such as benzene and toluene. Temperature is not critical to this process aspect and thus temperatures above and below room temperature can be employed.

The so-obtained compounds of formulae VI or VII can then be converted to the desired end products of formula I above by cleavage of the nitrogen protecting group; the conditions employed to effect this cleavage also result in the desired de-esterification. This cleavage can be accomplished following conventional techniques, as for example, by solvolysis using a mineral acid such as hydrochloric acid or an alkali metal base such as sodium hydroxide.

As is evident from the structure of the compounds of formula I above, these materials can exist in racemic form or in the form of their optically pure antipodes. Resolution of the racemic compound can be effected following conventional techniques including enzymatic techniques or salt formation with optically active amine bases or optically active carboxylic acids in conjunction with fractional crystallization.

The compounds of formula I above form pharmaceutically acceptable mono- and di-acid addition salts with organic and inorganic acids. Suitable inorganic acids for this purpose include the hydrohalic acids such as hydrochloric acid and hydrobromic acid, and other mineral acids such as sulfuric acid, phosphoric acid, nitric acid and the like. Suitable organic acids include mono- or polyacids such as benzoic acid, citric acid and the like.

The compounds of formulae I and IV above, or their pharmaceutically acceptable mono- or di-acid addition salts, inhibit ethylene production in plant tissues and therefor have utility as agents to retard the ripening of fruit shipment, to prolong the life of cut flowers and to prevent premature bud break in commerical fruit trees, thus avoiding frost kill.

The role of ethylene in the ripening of fruits has been recognized in the art for over thirty years. It is known that the production of ethylene in maturing fruits increases while the fruit separates from its pedicel. Conversely, it is known that an agent that will inhibit ethylene production will retard the ripening of fruit and thus is useful in prevention of spoilage of fruit during shipment. This knowledge can be utilized to demonstrate the efficacy of a compound in regard to its influence on fruit to inhibit the production of ethylene. Since apples can be considered a typical fruit representative of those amenable to treatment with a chemical agent that would retard ripening, the efficacy of the compounds of formula I above the inhibiting ethylene production may be illustrated with respect thereto.

The ability of the compounds of formulae I and IV above to inhibit ethylene production is demonstrated in the following test procedure. lg. slices of McIntosh applies were each placed on a separate 26 ml flint flask, containing 5ml of solution containing 0.4 M sucrose/0.1M sodium bisulfite and $1.25 \times 10^{-5}$ M of test compound.

Ethylene production in the reaction vessels was determined by gas liquid chromatography using a 1 ml sample. The results for this test procedure are reported in Table 1. These results show that the rate of ethylene production was greatly inhibited in the apple samples treated with the compounds of formula I. The results are expressed as the percent of ethylene produced as compared to the untreated control.

Table I

| Test Compound | % Ethylene Produced |
|---|---|
| Control | 100.0 |
| D,L-O-(N,N-diethylaminoethyl homoserine | 23.0 |
| Diethyl 2-(2-N,N-diethylaminoethoxy) ethyl phthalimidomalonate hydrochloride | 34.7 |

The compounds of formulae I and IV above, because of their ability to inhibit ethylene production in plant tissues are also useful in prolonging the life of cut flowers. This utility can be demonstrating in the following test procedures.

Freshly cut American Red Beauty Roses, with tightly closed but fully matured buds were used for the testing. The flowers were placed in 250 ml solutions containing 40 ppm of the test chemical. The control flowers were placed in distilled water. Three roses with 18 inch stem length were used for each treatment. The results are set forth in Table 2.

Table II

| Test Compound | Cut Life in Days |
|---|---|
| Control | 3–6 |
| D,L-O-(N,N-diethylaminoethyl) homoserine-40 ppm. | 5–8 |

The range in days indicates the cut life of the first and last flowers. These results show that the cut life of roses was extended when treated with the test compound, representative of the compounds of the present invention.

The following examples are illustrative of the present invention. All temperatures given are in degrees centigrade.

EXAMPLE 1

Preparation of diethyl 2-(2-chloroethoxy) ethylphthalimidomalonate excess bis-dichloroethyl 830g (5.8 mole) of bis-dichloroethyl ether, 118.7 g (0,362 mole) of sodium diethylphthalimido malonate and 96 g (0.58 mole) of potassium iodide were mixed and heated at 160° for 28 hours. The mixture was allowed to cool and the excessbis-dichloroethyl ether removed by steam distillation. The aqueous phase was extracted three times with 500 ml. methylene chloride. The methylene chloride phase was then washed with 500 ml. of water, dried over sodium sulfate, evaporated in vacuo and the residue treated with charcoal in ether. Crystallization from ethanol yielded the above-named product, as colorless crystals, m.p. 83°–85°.

EXAMPLE 2

Preparation of diethyl 2-(2-iodoethoxy) ethylphthalimido malonate 101.4 g (0.247 M) of diethyl 2-(2-chloroethoxy) ethyl phthalimido malonate and 185 g (1.235 M) of ground sodium iodide were dissolved in 1,200 ml of acetone and heated at reflux for 4 ½ days. The reaction mixture was filtered, 74 g (0.494 M) of sodium iodide was added, and the mixture heated at reflux for another 24 hours. The reaction mixture was then filtered and evaporated in vacuo. The sodium chloride precipitate was washed with ether, the ether phase filtered and the ether evaporated in vacuo. The residue was treated with charcoal in ether. Crystallization from ethanol yielded the above-named product as colorless crystals, m.p. 62°–64°.

EXAMPLE 3

Preparation of N-ethyl-N'-[1,1-diethoxy-carbonyl-3-(2-iodoethoxy)-propyl]phathalamide 48.8 g (97.2 mmoles) of diethyl 2-(2-iodoethoxy) ethylphthalimido malonate was dissolved in 300 ml of methylene chloride and chilled to −78°. 63.5 ml (912 mmoles) of ethylamine was added and the reaction mixture was stirred at −78°for 3 ½ hours. The mixture was then allowed to warm to 0° over a period of 2 hours and kept at that temperature for 3 ½ hours. The reaction mixture was evaporated in vacuo (bath temperature at room temperature) and the resulting oil was dried in high vacuo. The residue was dissolved in ether and the insoluble oil extracted with ether and filtered. The residue was treated with charcoal in ether, filtered and evaporated in vacuo. Crystallization from ether/petroleum ether yielded the above-named product as colorless crystals, m.p. 94°–96°.

EXAMPLE 4

Preparation of D,L-O-(N-ethylaminoethyl) homoserine 33.2 g (60.6 moles) of N-ethyl-N+-[1,1-diethoxycarbonyl-3-(2-iodoethoxy propyl] phthalamide was dissolved in 140 ml of methylene chloride and 60 ml of ethylamine and stirred at room temperature for 5 days. The reaction mixture was evaporated in vacuo, the residue was dissolved in methylene chloride, the salt filtered and washed with methylene chloride. The filtrate was evaporated in vacuo and dried in high vacuo. The resulting oil was dissolved in 100 ml of ethanol and 200 ml. of 5N NaOH and heated at reflux for 2 hours. The ethanol was evaporated in vacuo. The aqueous phase was acidified with 6N HCl to PH1 and evaporated in vacuo. The salt was then dissolved in 640 ml of 6N HCl and heated on a steam bath for 3 hours. The reaction mixture was filtered and evaporated in vacuo. The residue was applied to 500 ml of Bio-Rad (AG -50W-X4) (50-100 mesh) cation exchange resin in the $H^+$ form. The resin was eluted with 1,000 ml of water, 1,000 ml of 20% pyridine and 1,500 ml. 1N ammonium hydroxide. The latter eluate was evaporated in vacuo, the oil dissolved in a small amount of water and acidified with 6N HCl to pH5 and evaporated in vacuo, dissolved in ethanol and filtered. Crystallization was affected by adding ether yeilding the above-named product as colorless crystals, m.p. 100°–105°.

EXAMPLE 5

Preparation of diethyl 2-(2-N,N-diethyl-aminoethoxy)ethylphthalimidomalonate hydrochloride 50.3 g (100 mmoles) of diethyl 2-(2-iodoethoxy) ethylphthalimido malonate, 100 ml. of diethylamine and 900 ml of toluene were mixed and heated at 60° for 64 hours. The reaction mixture was filtered and evaporated in vacuo. The residue was dissolved in ether, filtered, heated with charcoal, filtered and evaporated in vacuo. The oil was dried in high vacuo. The oil was dissolved in ether, treated again with charcoal and filtered through celite. Hydrogen chloride gas (dried by passing through $H_2SO_4$ and $CaCl_2$) was introduced. The precipitated oil was scratched until crystallization was effected. The salt was washed with ether, and recrystallized from ethanol/ether yielded the above-named product as colorless crystals, m.p. 140°–142°.

EXAMPLE 6

Preparation of D,L-O-(N,N-diethylamino-ethyl) homoserine 21.85 g (45 mmoles) of diethyl-2-(2-N,N-diethylaminoethoxy) ethyl-phthalimidomalonate hydrochloride was dissolved in 80 ml of ethanol to which was added 160 ml of 5 N Na OH. The reaction mixture was stirred and heated at reflux for 1 hour. The ethanol was allowed to boil off. The aqueous phase was acidified with 6 N HCl to pH 1 and evaporated in vacuo. The salt was dissolved in 480 ml of 6N HCl and heated at 100° for 90 minutes. The reaction mixture was evaporated in vacuo. The residue was dissolved in water and applied to 400 ml Bio-Rad (Ag-50W-X4) (50–100 mesh) cation exchange resin in the $H^+$ form. The resin was eluted with 1,000 ml of water, 1,000 ml of 20% pyridine in water and 1,500 ml of 1N ammonium hydroxide. The ninhydrin active material from the ammonium hydroxide fraction was collected and evaporated in vacuo. The resulting oil was dried under vacuum, dissolved in water, acidified with 6N HCl to pH5 and evaporated in vacuo to yield residue A.

The material from the 20% pyridine in water fraction was evaporated in vacuo to give 7.721 g. of material. This was dissolved in 25 ml. of ethanol and 50 ml of 5N NaOH and heated at reflux for 1 hour. The ethanol was removed in vacuo. The aqueous phase was acidified with 6N HCl to pH1 and evaporated in vacuo. The salt was dissolved in 160 ml of 6N HCl and heated at 100° for 2 hours. The reaction mixture was evaporated in vacuo. The residue was dissolved in water and applied to 150 ml of Bio-Rad (AG-50W-X4) (50–100 mesh) cation exchange resin in the $H^+$ form. The resin was eluted with 1,000 ml of water, 300 ml of 20% pyridine in water and 500 ml of 1N ammonium hydroxide. The ammonium hydroxide fraction was evaporated in vacuo, dissolved in 50 ml 6N HCl evaporated in vacuo. The oil was dissolved in ethanol, filtered, evaporated and dried under vacuum to yield residue B.

The material from residue A and from residue B above was combined and dried over $P_2O_5$ under high vacuum for 1 week. The above-named product was thereby obtained as a colorless, hygroscopic foam.

We claim:

1. A compound of the formula

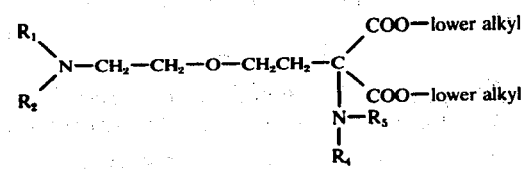

wherein $R_1$ and $R_2$ are lower alkyl; and $R_4$ and $R_5$ taken together with their attached nitrogen atom form the phthalimido group.

* * * * *